US010337317B2

(12) United States Patent
Foss et al.

(10) Patent No.: US 10,337,317 B2
(45) Date of Patent: Jul. 2, 2019

(54) WAX TRACERS

(71) Applicant: Institutt for Energiteknikk, Kjeller (NO)

(72) Inventors: Martin Foss, Skedsmokorset (NO); Tor Bjørnstad, Hagan (NO); Terje Sira, Skedsmokorset (NO)

(73) Assignee: Institutt for Energiteknikk, Kjeller (NO)

( * ) Notice: Subject to any disclaimer, the term of this patent is extended or adjusted under 35 U.S.C. 154(b) by 126 days.

(21) Appl. No.: 15/512,202

(22) PCT Filed: Sep. 18, 2015

(86) PCT No.: PCT/EP2015/071448
§ 371 (c)(1),
(2) Date: Mar. 17, 2017

(87) PCT Pub. No.: WO2016/042133
PCT Pub. Date: Mar. 24, 2016

(65) Prior Publication Data
US 2017/0292369 A1    Oct. 12, 2017

(30) Foreign Application Priority Data

Sep. 18, 2014  (GB) .................................. 1416526.0
Sep. 18, 2014  (NO) .................................. 20141132

(51) Int. Cl.
*E21B 47/10* (2012.01)
*C09K 8/524* (2006.01)
(Continued)

(52) U.S. Cl.
CPC .......... *E21B 47/1015* (2013.01); *C09K 8/524* (2013.01); *E21B 49/08* (2013.01);
(Continued)

(58) Field of Classification Search
CPC ..... C09K 8/524; E21B 47/1015; E21B 49/08; G01N 21/64; G01N 21/643;
(Continued)

(56) References Cited

U.S. PATENT DOCUMENTS 5,047,632 A * 9/1991  Hunt ....................... E21B 27/02
                                                         250/259
5,474,937 A * 12/1995 Anderson, II ......... C06B 23/008
                                                         436/139
(Continued)

FOREIGN PATENT DOCUMENTS

EP    2743326 A1   6/2014
WO    9315398 A1   8/1993
(Continued)

OTHER PUBLICATIONS

Khalil et al. Abstract from Proceedings—SPE International Symposium on Oilfield Chemistry, Houston, Feb. 16-19, 1999.*
(Continued)

*Primary Examiner* — Maureen Wallenhorst
(74) *Attorney, Agent, or Firm* — Christopher & Weisberg, P.A.

(57) ABSTRACT

A method for monitoring precipitation of a wax component in a hydrocarbon fluid stream
  i) using a labelled wax introduced in a fluid transport system at one in-flow point and measuring its absolute or relative concentration at one out-flow point is provided. A method for generating a labelled wax, and the use of a labelled wax is also provided.

17 Claims, 5 Drawing Sheets

Principle sketch of flow loop for study of wax deposition and qualification of wax tracer molecules.

(51) Int. Cl.
*E21B 49/08* (2006.01)
*G01N 21/64* (2006.01)
*G01N 33/24* (2006.01)
*G01N 33/28* (2006.01)

(52) U.S. Cl.
CPC ......... *G01N 21/643* (2013.01); *G01N 33/241* (2013.01); *G01N 33/2823* (2013.01); *Y10T 436/13* (2015.01); *Y10T 436/21* (2015.01)

(58) Field of Classification Search
CPC .......... G01N 2021/6439; G01N 33/24; G01N 33/241; G01N 33/2823; Y10T 436/13; Y10T 436/21; Y10T 436/214
USPC .......... 436/25, 27, 28, 56, 60, 139, 141, 172
See application file for complete search history.

(56) References Cited

U.S. PATENT DOCUMENTS

| | | | |
|---|---|---|---|
| 7,469,597 B2* | 12/2008 | Flaten | G01F 22/00 73/861.04 |
| 7,560,690 B2* | 7/2009 | Stray | E21B 47/1015 250/303 |
| 2009/0233817 A1* | 9/2009 | Kriegel | C10L 1/2364 507/90 |
| 2016/0010454 A1* | 1/2016 | Sira | E21B 47/1015 73/152.29 |
| 2016/0168952 A1* | 6/2016 | Qu | C09K 8/524 356/316 |

FOREIGN PATENT DOCUMENTS

| | | | |
|---|---|---|---|
| WO | 2006004426 A1 | | 1/2006 |
| WO | 2015/097116 | * | 7/2015 |

OTHER PUBLICATIONS

International Search Report and Written Opinion dated Nov. 11, 2016 for corresponding International Application No. PCT/EP2015/071448 International Filing date: Sep. 18, 2015 consisting of 10-Pages.

* cited by examiner

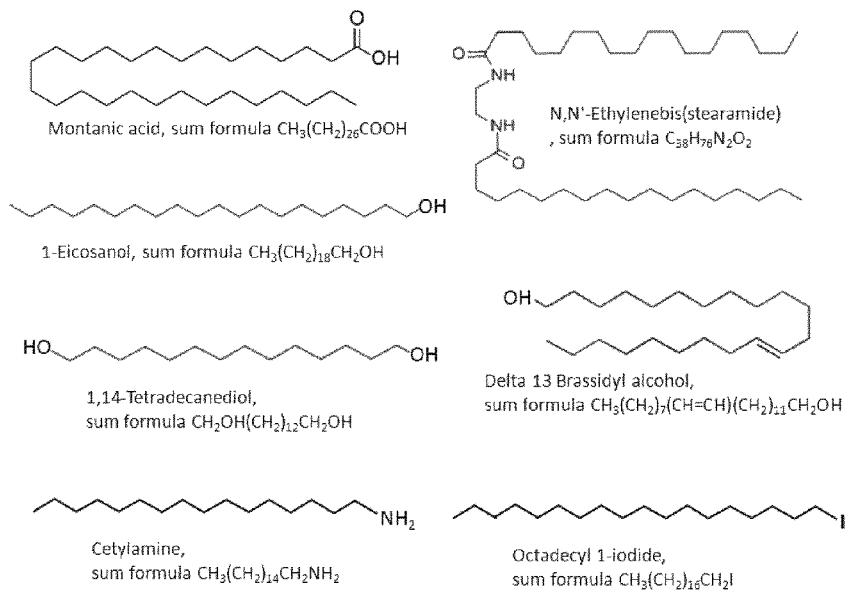
Figure 1: Examples of molecular classes which can be used as precursors for labelling operations.
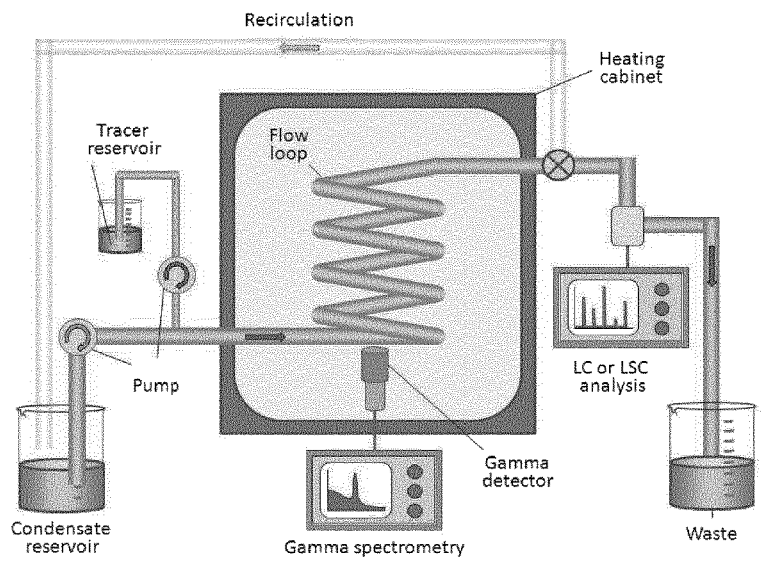
Figure 2: Principle sketch of flow loop for study of wax deposition and qualification of wax tracer molecules.

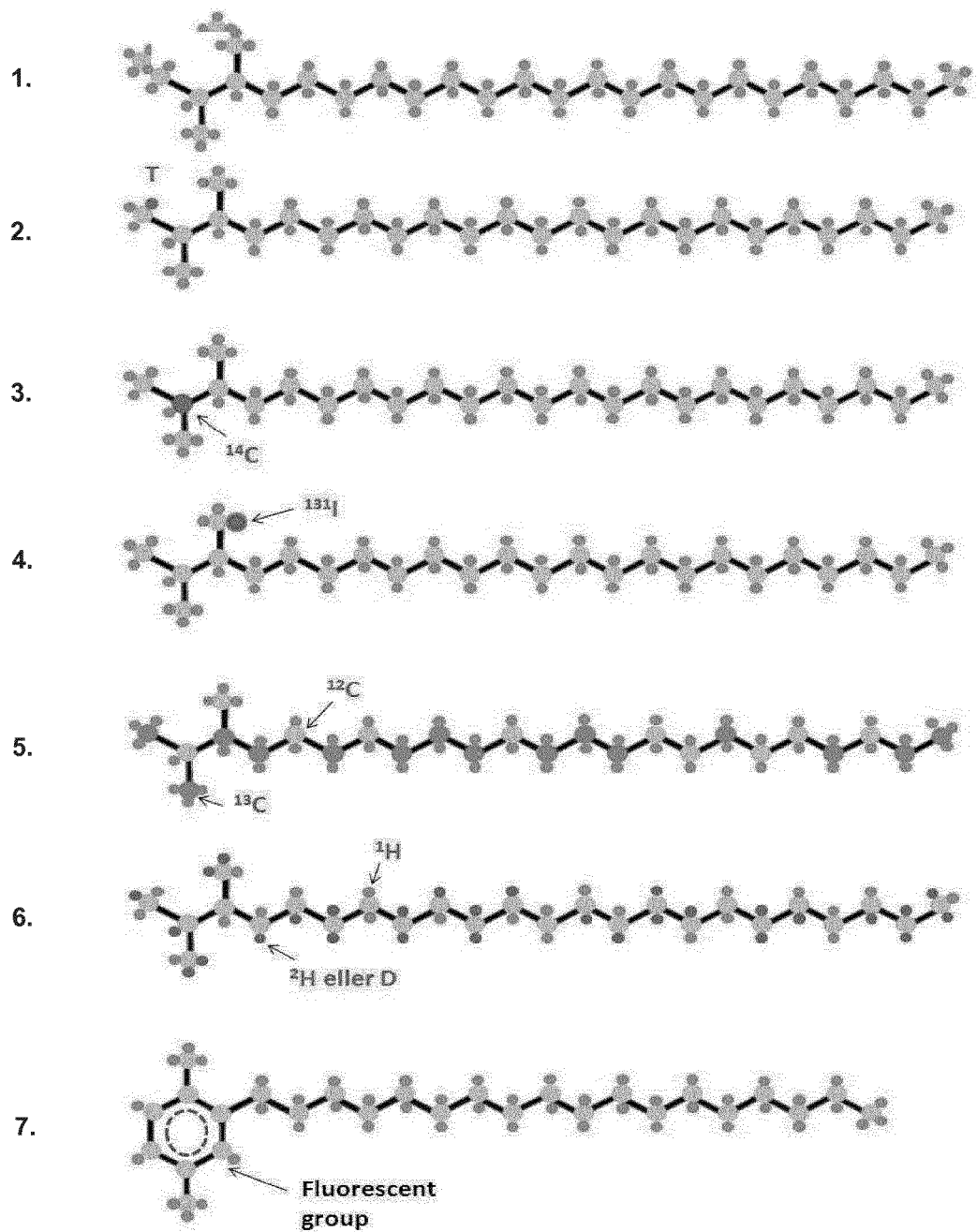
Figure 3 - some example labelling methods. 1. is unlabelled. 2-7 show various labelling methods.

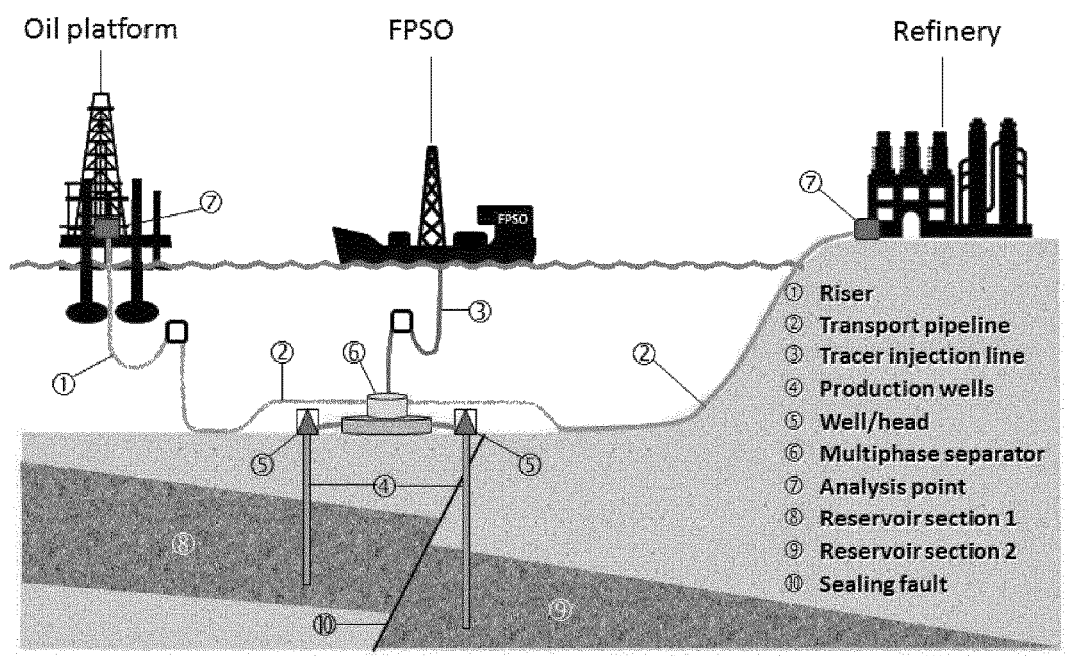
Figure 4: The figure shows one potential layout of a production system.

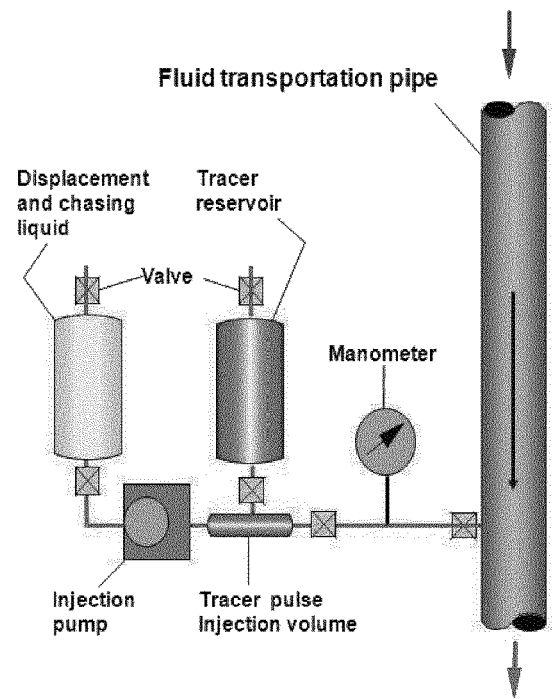
Figure 5a. Sketch of wax tracer pulse injection system.
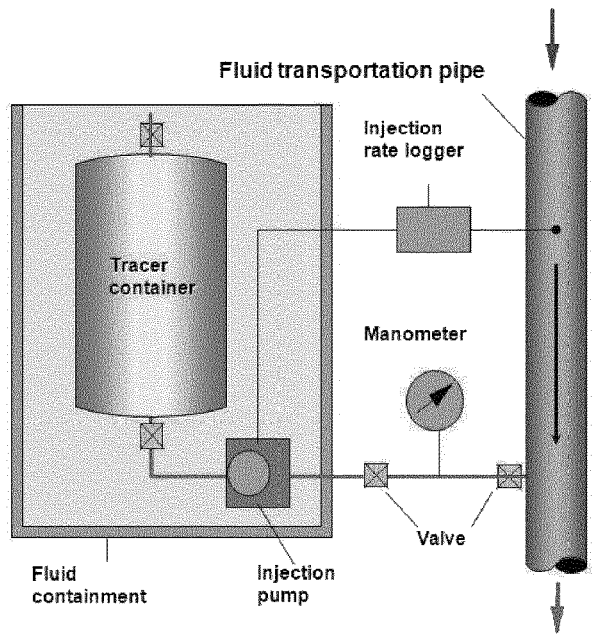
Figure 5b. Sketch of wax tracer injection system for continuous constant concentration injection.

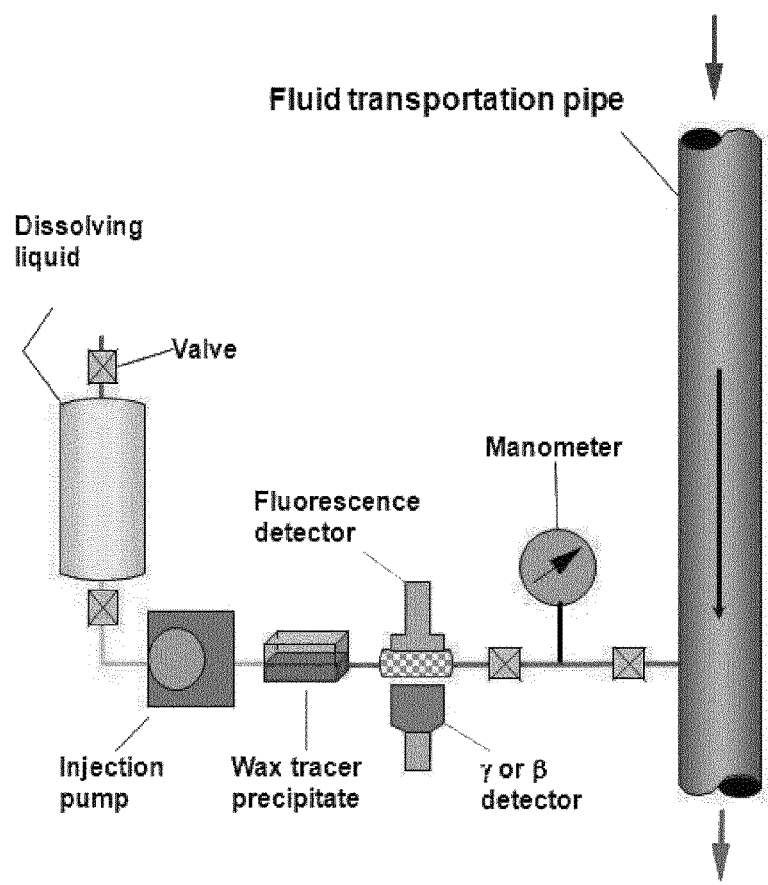
*Figure 5c. Sketch of wax tracer injection system for continuous dissolution of preformed wax precipitate containing wax tracer molecules with detectors for continuous logging of injected tracer concentration.*

WAX TRACERS

CROSS-REFERENCE TO RELATED APPLICATIONS

This application is a Submission under 35 U.S.C. § 371 for U.S. National Stage Patent Application of, and claims priority to, International Application Number PCT/EP2015/071448, filed Sep. 18, 2015, entitled "WAX TRACERS", which is related to and claims priority to Great Britain Application Number 1416526.0, filed Sep. 18, 2014, and Norwegian Application Number 20141132, filed Sep. 18, 2014, the entire contents of all three of which are hereby incorporated herein by reference.

FIELD OF THE INVENTION

The present invention relates to the monitoring of wax deposition and precipitation in pipelines and other equipment used in the handling and transport of fluids produced from a subterranean reservoir. In particular, the invention relates to the monitoring of wax precipitation in process equipment where such wax is deposited or potentially deposited from a hydrocarbon-containing fluid produced from a subterranean reservoir.

BACKGROUND TO THE INVENTION

Development and transportation of oil and gas fields in increasingly difficult areas pose significant challenges. This includes a significant portion of the subsea fields under development today. One of the most challenging issues is wax deposition inside the transportation and production tubing. This issue is regarded as one of the main flow assurance subjects in subsea and cold climate production where the produced fluids are cooled to below the wax appearance temperature for the fluids [1]. The wax appearance temperature is a property of the oil and can be as high as 65° C. In recent years there has been a significant research effort on the understanding of the deposition and the mitigation of waxing [1-4]. The composition and properties of the wax itself has been quite well understood but a remaining challenge is the monitoring of the wax initiation and growth in the production tubing and equipment. The use of pigs and pressure loss is typically used to monitor pipelines [2, 5]. The problem with pigging inspections is the significant amount of work required to run a pigging operation which might interrupt or possible stop the production temporarily. Pressure loss measurements are typically not sensitive enough to pick up deposition until the deposition has formed a significantly thick layer on the walls of the pipeline.

It would evidently be of considerable value to provide a method by which waxing initiation and/or the extent of waxing can be determined and/or monitored before waxing has reached the severity required to cause a measurable drop in pressure or flow. In particular, if waxing initiation can be detected before a significant layer has built up on the transport system, such as the pipeline or valves, chokes etc thereof then mitigation measures may be used prior to waxing becoming a significant problem. Equally, where waxing might be an issue then mitigation measures can be avoided unless or until initiation of waxing takes place. In such situations the cost and complexity of mitigation measures can be avoided or postponed.

The present inventors have now established that by use of selected labelled waxes or wax-like molecules, a method can be provided to significantly improve the sensitivity and ease by which the onset and growth of wax can be monitored. The authors thus herein disclose a novel method for wax tracing.

In addition to the abovementioned novel wax tracing method, the same monitoring technique can be used for monitoring of precipitation of asphaltenes.

SUMMARY OF THE INVENTION

In a first aspect the invention provides a method for monitoring precipitation of at least one wax component from a hydrocarbon-containing fluid stream during the flow of said fluid stream through a fluid transport system having at least one in-flow point and at least one out-flow point, said method comprising:
i) introducing at least one labelled wax into said hydrocarbon-containing fluid stream at at least one in-flow point; and
ii) measuring the relative or absolute concentration of said labelled wax in at least one sample taken at at least one out-flow point.

Key optional steps in such a method include additionally:
a) taking a sample of said hydrocarbon-containing fluid stream (e.g. at the in-flow point);
b) analysing the sample of said hydrocarbon-containing fluid;
c) identifying the structure and/or molecular weight of at least one wax component in said sample of said hydrocarbon-containing fluid;
d) selecting or generating at least one labelled wax based upon at least one wax component identified in step c);
e) utilising the at least one labelled wax selected or generated in step d) as the at least on labelled wax in step i);
wherein steps a) to d), if included, are carried out prior to steps i) and ii).

As used herein the labelled wax is used as a tracer in measuring the precipitation of wax in the fluid transport system. The term "tracer" is therefore used herein to indicate a labelled wax. Evidently, the in-flow and out-flow points referred to herein will be points on the fluid transport system where material can be introduced and extracted respectively. In both cases, these may be at an end of the fluid transport system, for example at the beginning (e.g. wellhead) or end of a pipeline respectively. Equally, such in-flow and out-flow points may be positioned at any appropriate points along the fluid transport system. At least one in-flow point will be up-stream of at least one out-flow point but many combinations of in- and out-flow points may be usefully employed. Where more than one in-flow point is utilised, the same tracer may be used at each or preferably a unique tracer will be introduced at each in-flow point.

In one key embodiment, the absolute or relative concentration measured at step ii) may be compared to one or more threshold values. Where wax is depositing within the transport system then the labelled wax component concentration will fall during transport and thus by comparing to one or more threshold values a decision can be made regarding the degree of wax precipitation occurring. Thus the method of the invention may additionally comprise undertaking at least one wax mitigation measure when the relative or absolute concentration measured in step ii) falls below a threshold value. Evidently more than one threshold may be used and in such a case each may indicate a need for one or more wax mitigation measures.

By monitoring waxing using any of the methods of the present invention, an ongoing measure of the degree of waxing may be established. This may be formed, for example, by sampling periodically or continuously and multiplying the concentration of labelled wax by the time between samples or measurements to give an approximate integral or area-under-curve for wax precipitation against time. The method of the invention may thus comprise additionally undertaking at least one wax mitigation measure when the area under a curve (integral) of relative or absolute concentration measured in step ii) against time for a predetermined period falls below a threshold value. Again it will be evident that more than one threshold may be used and more than one mitigation measure may be deployed depending upon which threshold is crossed.

Suitable wax mitigation measures appropriate for any aspect of the present invention comprise at least one of: starting or increasing the addition of at least one de-waxing component to said hydrocarbon-containing fluid stream; mechanically de-waxing (for example pigging) at least a part of said fluid transport system; or thermally de-waxing at least a part of said fluid-transport system.

An important contribution of the present invention is the facility to generate labelled waxes that may co-precipitate with wax components in a hydrocarbon-containing fluid stream. In a further aspect the invention therefore provides a method for the generation of at least one labelled wax comprising:
 a) taking a sample of a hydrocarbon-containing fluid stream (e.g. at an in-flow point) of a fluid transport system;
 b) analysing the sample of said hydrocarbon-containing fluid;
 c) identifying the structure and/or molecular weight of at least one wax component in said sample of said hydrocarbon-containing fluid;
 d) selecting a wax based upon at least one wax component identified in step c);
 e) covalently or isotopically modifying the structure of the selected wax with at least one label.

In a still further aspect the invention additionally provides the use of at least one labelled wax to monitor precipitation of at least one wax component from a hydrocarbon-containing fluid stream during the flow of said fluid stream through a fluid transport system having at least one in-flow point and at least one out-flow point. Such a labelled wax may be a wax generated by any of the methods described herein. Such a use may be according to any of the methods described herein. Such generation may be by modification of a purified or commercial wax component or by synthesis of the labelled wax(es) from an appropriate starting material.

Where an aspect of the present invention involves a step of taking a sample of a hydrocarbon-containing fluid stream for analysis (e.g. step a) in any of the above aspects), such sampling may be made at any representative point in terms of both position and time. The most preferable point for sampling will typically be at the in-flow point of the relevant fluid transport system because such a sample will accurately reflect the flow of material actually entering the transport system. However, where appropriate and/or convenient, such sampling may take place at other points (including those described herein). These include at one or more out-flow points or at any other point along the fluid transport system (e.g. where the system can be readily accessed) and/or at another point where the hydrocarbon-containing fluid is accessible, such as within a formation, at a production point. This may be during production or may be prior to full-scale production, such as at an exploration or development stage. Such samples taken at a pre-production stage may allow appropriate labelled waxes to be developed, synthesised chosen and/or purchased in readiness for use in protecting the fluid-transport system.

DETAILED DESCRIPTION OF THE INVENTION

The invention relates to the monitoring of wax deposition and precipitation in pipelines and other equipment. The technique is simple and efficient and can be used for early detection of the onset of deposition. The technique can be utilized on existing fields where an injection line to the wellhead is installed (MEG injection lines, inhibitor injection lines etc.). The basis for the invention is to inject a selected labelled wax (which may be a true labelled wax or a labelled wax-like molecule, both of which are referred to as a "labelled wax" herein where context allows) with properties specifically chosen to enable the product to precipitate alongside the wax component precipitating from the solution. By measuring the residual concentration of the product, information regarding onset and growth of wax can be monitored by periodic, frequent or continuous measurements. In one embodiment the wax component may be tailored to the specific produced mixture and the waxes present therein. By appropriate choice of one or more wax components, the method will be able to detect deposition of a wide range of waxes with different chemical compositions. This method where tracers are used is especially suited for fields where sampling at the wellhead is difficult, such as subsea fields. Oil samples from the well are typically only taken before production is started.

During field development at a hydrocarbon reservoir, such as an oil field, oil is sampled from the reservoir. By careful characterization of relevant samples a description of the oil components can be obtained. This knowledge can then be used to determine the quantity and type of components forming wax in the production systems.

Waxes are alkanes (saturated hydrocarbons) typically heavier than C18 (such as C20-C100 [7]) that are produced as part of the hydrocarbon phase in oil and gas-condensate production. These components of the oil are subject to precipitation due to changes in solubility (temperature, pressure, compatibility issues) and will, if deposited on the interior of pipelines, separators, chokes or other types of process equipment, cause significant production upsets [5]. Being able to monitor the amount of wax travelling from the wellhead throughout the system is therefore a significant advantage since deposition and risk of damage or blockage of the production system can be detected. Knowing when wax deposition is initiated would greatly improve the cost efficiency of the mitigation methods deployed to handle the wax. Detection of wax onset allows countermeasures to be set in place before the wax deposition becomes unmanageable. Typical spots where wax might precipitate include areas with changes in turbulence (separators etc.), temperature (cold spots etc.), pressure (choke etc.), chemistry (injection points etc.) and surface properties (process equipment).

As used herein, the term "wax-like molecules" is used to indicate molecules that have similar structure and/or function to a true wax, but may include other chemical characteristics not typically seen in a "true" wax. Preferred wax-like molecules will also include a significant number of saturated carbon centres, such as at least 12 or at least 16 saturated (sp3) carbon centres. This will preferably be at least 18 (such as 20 to 100) saturated carbons. Where there are n carbons in a wax-like molecule, there will typically be around 2n (e.g. between 2n+2 and 2n−10, where n is 12 or greater as indicated above) hydrogens bound to carbon. The carbon chains of a wax-like molecule may be linear, branched and/or cyclic but will confer the "waxy" nature of the molecule due to the hydrophobic and non-polar nature of the carbon chain and the large number of carbon-hydrogen bonds.

Wax-like molecules may also contain a small number (e.g. 0 to 5, preferably 1 to 4) of functional groups. Most preferable numbers of functional groups are 1, 2 or 3, particularly 1 or 2. These may be hydrocarbon groups such as double-bonds (alkene moieties), triple bonds (alkyne moieties), and/or aromatic rings. Alternatively, or in addition, the functional groups may be hetero-atom containing functional groups such as halogens (e.g. Cl, Br, I), amides, esters, ethers, amines, alcohols, carboxylic acids and/or ketones. Typically no more than 5 heteroatoms (ie non-hydrocarbon atoms) will be present in any wax-like molecule, preferably no more than 3, and most preferably 0, 1 or 2 heteroatoms will be present. The most common heteroatoms will be halogens, oxygen, nitrogen, sulphur and/or phosphorous, particularly oxygen and/or nitrogen. Wax-like molecules may be labelled for use in the present invention, as described herein.

Ability to measure onset of wax deposition or changes in wax deposition rate in detail will be critical for several situations in pipelines or process equipment. Examples of situations where monitoring is useful are:
  When system changes are made with respect to changes in conditions such as pressure and temperature. This includes shut-down, start-up, choke changes, pigging etc. Pressure and temperature change may lead to precipitation also in the near-well area. The solubility of wax is a strong function of pressure.
  When the chemistry is changed in the system. This might be due to operations such as chemical injection to mitigate other production issues (emulsions, flow improvers, inhibitors etc.), new tie-ins, EOR operations.
  When the composition of the produced fluids change. This includes changes in the fluid composition due to late life pressure decrease in the reservoir and changes to the reservoir temperature.

Thus, for example, the method of the invention may be used continuously or periodically (as described herein) for at least 1 month, preferably 6 months or 1 year following an event which changes the conditions of the fluid or fluid transport system. Such events include those described herein, such as a change or partial change in source of the hydrocarbon-containing fluid stream; the addition, removal or replacement of at least one element of the fluid transport system; the addition, removal or change in concentration of at least one additive introduced into the hydrocarbon-containing fluid stream; or a change in conditions of temperature and/or pressure at at least one point on the fluid transport system.

References herein to a "fluid transport system" relate to any system of one or more components which may be used to transport a hydrocarbon-containing fluid (particularly a fluid comprising oil). Typical components comprised in such a fluid transport system include pipes (e.g. a pipeline), valves, chokes, filters, mixers, separators (test, sand or phase separators), joints and/or thermal expansion joints.

One alternative to the use of tracer would be to use a chemical analysis technique such as GC-MS/MS to monitor the actual wax produced from the well. In order to use GC monitoring regular sampling at the wellhead would be required. Sampling from the wellhead is, however, not feasible for most subsea fields, due to high cost, and the technique would therefore be difficult and expensive to implement. The operation of a GC-MS analyzing technique for single components in the oil is also not trivial and would probably not be feasible offshore. The use of this technique is further complicated by mixing of fluids from different wells which would require even more sampling points at the wellheads.

In the present invention various "tags" or "labels" (the terms are used herein equivalently) are employed to allow the wax component to be detected. Such labels may be detected by any suitable method but preferred examples include:
  one or more existing atoms of the wax or wax-like molecule is exchanged with another stable or radioactive isotope of the same chemical element,
  exchange of an atom (especially a hydrogen atom) with a radioactive isotope of another "foreign" chemical element without changing the main properties of the molecule or
  covalently attach a chemical group with measurable properties, for instance, special fluorescent properties.

Examples of these types of labels include, without limitation, the following:

Same-element substitution:
  Tritium (T or $^3$H) to substitute one or more $^1$H-atoms in the molecule,
  $^{14}$C to substitute one or more stable $^{12}$C-atoms in the molecule,
  $^{35}$S if the wax molecule contains sulphur or
  $^{32}$P if the molecule contains phosphorous.

These are all beta emitters and are best analysed with liquid scintillation counting (LSC) after sampling. On-site analysis is possible.

Different element radioactive substitution:
  Halogene isotopes where the most preferable are $^{125}$I and $^{131}$I. In some cases one may regard also 82Br, but its half-life of 35 hours may, in some cases, be too short.

These are all beta emitters with associated and specific gamma radiation. Analysis can be performed with gamma spectroscopy after sampling, but the gamma radiation also offers the possibility of analyzing the tracers continuously, non-destructively and on-line directly in the gas stream through the non-transparent tubing wall. On-site analysis is possible.

Same Element Isotopic substitution:
  Stable isotopes of hydrogen and/or carbon, and these are deuterium (D or $^2$H) and $^{13}$C. Possible, but less preferred, is the labeling with $^{15}$N if the molecule originally contains nitrogen,
  $^{18}$O if the molecule originally contains oxygen or
  $^{34}$S if the molecule contains sulphur.

In the case of isotopic substitution with isotopes of elements other than C or H, a majority of the stable atoms in the selected wax molecule tracer will have to be exchanged with their corresponding mentioned isotopes. In the case of Hydrogen or carbon, it remains preferable to have multiple substitutions such as at least 10% preferably at least 25%, more preferably at least 50% of the relevant atoms. For instance, it may be necessary to substitute more than half of all hydrogen atoms with deuterium in order to achieve the needed analytical sensitivity. Such molecules are analysed, after collection and combustion, with isotope mass spectrometry in a laboratory environment.

Optically detectable labels:
  A molecular group with fluorescent properties. This most often involves double bonds and Pi-orbitals (π-electrons). FIG. 3.7. below shows an example of such a fluorescent group. The compounds can be analysed with high sensitivity by laser-induced fluorescence, both after sampling and possibly also in situ (instream). If molecular separation is required, it may be accomplished by the use of LC with reversed phase or size exclusion columns. Other fluorescent labels are well known, for example from:

Table of fluorophores: http://pingu.salk.edu/flow/fluo.html

Database of fluorophores: http://www.fluorophores.tu-graz.at/substance/Candidate wax molecules for covalent labelling:

The waxy molecules to be covalently labelled should either be halogenated or contain functional group(s) like —OH, —COOH, —NH$_2$. The waxy molecules may also be esters which can be hydrolysed to create —OH or —COOH- functional groups for subsequent labelling.

Typical examples from various wax molecules carrying appropriate functional groups are given in FIG. 1 below.

In one aspect the present invention relates to a method of generating at least one labelled wax. This may be achieved by the methods disclosed herein utilising chemistry known in the art. One particularly suitable method is by the modification of fatty alcohols.

Fatty alcohols are especially versatile for further labelling. Table 1 indicates briefly the conversion reactions which may be used to convert an alcohol into a set of other waxy components. The type of reagent is listed in the middle column and the resulting functional group on the right. Labelling may take place through the reactants which may contain the tracer tag (e.g. an heavy or radioactive isotope) or may carried out by means of a further reaction (e.g. covalent bonding of a fluorophore to an acid group):

TABLE 1

General reactions with fatty alcohols

| Fatty alcohol + | +Oxygen | ⇒ aldehydes and/or carboxylic acids |
|---|---|---|

TABLE 1-continued

General reactions with fatty alcohols

| | +Alkali melt | ⇒ carboxylic acids |
|---|---|---|
| | +Alkyne | ⇒ Vinyl ether |
| | +Carboxylic acid | ⇒ Ester |
| | +Hydrogen halide | ⇒ Alkyl halide |
| | +Ammonia/Amine | ⇒ amines |
| | +Aldehyde/Ketone | ⇒ acetals |
| | +Sulfide | ⇒ Thiols |
| | +Alkoholate/H$_2$S | ⇒ Xanthates |
| | +Metals/Metal halides | ⇒ Metal alkoxides |

It is important to ensure that the resulting labelled waxy molecule is representative for a defined wax molecular range with respect to deposition temperature. Also, thermal and/or microbial stability and possible interactions (or lack of such) with surrounding material must be examined in dedicated laboratory experiments. Thermal stability is checked in static batch experiments extended over time where sealed glass ampoule samples of the labelled molecules are subjected to various temperatures ranging from a few ° C. to 50-60° C. under gentle shaking. Samples are extracted as a function of time for analysis of the "remaining" concentration of tracers. In this temperature range, the biodegradation is the most probable degradation mechanism. If analysis is carried out with GC, the molecules have to be sufficiently stable at temperatures>300° C. in order to conduct the analysis. However, GC analysis is most practical for the precursor wax molecule while LC at moderate temperatures will be the analytical method of choice for the tracer molecules labelled with a non-radioactive fluorescent label.

As discussed above, three primary methods are considered as examples of suitable molecular labels/tags: The primary examples are radioactive nuclides, stable (less common, especially heavy) isotopes and optically detectable (fluorescent) groups. Further description of the properties of these tags is provided below.

The Radioactive Labels

The relevant nuclear properties of the most practical radionuclides for this kind of labelling are given in table 2 below.

TABLE 2

Nuclear data for the candidate radionuclide labels

| Radionuclide | Half-life | Radiation type and energy (absolute intensity in brackets) | Production method | Comments |
|---|---|---|---|---|
| $^3$H (T) | 12.32 y | Soft β$^-$-emission: $E_{\beta max}$ = 18 keV (100%) | Thermal n-reactions: 1: $^3$He(n,p)$^3$H 2: $^6$Li(n,α)$^3$H Commercially available | Some hydrogen ($^1$H) atoms, as a natural component in all hydrocarbons, can be substituted with T ($^3$H) |
| $^{14}$C | 5730 y | Relatively soft β$^-$-emission: $E_{\beta max}$ = 156.5 keV (100%) | Reactor neutron reaction: $^{14}$N(n,p)$^{14}$C Commercially available | A carbon ($^{12}$C), as a natural component in all hydrocarbons, can be substituted with $^{14}$C |
| $^{32}$P | 14.26 d | Higher-energy β$^-$-emission: $E_{\beta max}$ = 1710.7 keV (100%) | Reactor irradiation: $^{35}$Cl(n,p)$^{35}$S | The relevance of the $^{32}$P-label depends on the molecular content of phosphorus, either naturally occurring or introduced. For instance phosphate (—O—PO$_3$H$_2$) or phosphonate (—PO$_3$H$_2$) groups. Highly suitable for molecules naturally containing phosphorus |

TABLE 2-continued

Nuclear data for the candidate radionuclide labels

| Radio-nuclide | Half-life | Radiation type and energy (absolute intensity in brackets) | Production method | Comments |
|---|---|---|---|---|
| $^{35}$S | 87.5 d | Relatively soft $\beta^-$-emission: $E_{\beta max} = 167.3$ keV (100%) | Reactor irradiation: 1: $^{35}$Cl(n,p)$^{35}$S 2: $^{34}$S(n,$\gamma$)$^{35}$S Commercially available | The relevance of $^{35}$S-label in a wax molecules depends on its possible content of S-atoms, either naturally occurring or introduced. For instance in attached sulphate (—O—SO$_3$H) or sulphonic acid (—SO$_3$H) groups. Highly suited for molecules naturally containing sulphur. Might be used as a substitute for oxygen (e.g thiol in place of alcohol) |
| $^{82}$Br | 35.34 h | $\beta^-$-emission: $E_{\beta max} = 444$ keV (98.6%) $\gamma$-radiation-main energi-es in keV: 776.5 (83.5%), 554.3 (70.8%), 619.1 (43.4%), 1044.0 (27.2%) | Reactor irradiation: $^{81}$Br(n,$\gamma$)$^{82}$Br | The relevance of $^{82}$Br-label in a wax molecule depends on its possible content of halogen atoms either naturally occurring or (more likely) where a substitution can be made without affecting waxing properties. |
| $^{125}$I | 59.41 d | Electron capture (EC = 100%) $\gamma$-radiation in keV: 35.5 (6.7%) strongly converted $\Rightarrow$ conversion electrons | Examples of reactions: 1: $^{123}$Sb($\alpha$,2n)$^{125}$I 2: $^{126}$Te(p,2n)$^{125}$I 3: $^{124}$Xe(n,$\gamma$)$^{125}$Xe $\Rightarrow$ $\beta^+$ decay to $^{125}$I Commercially available | The relevance of $^{124}$I-label in a wax molecule depends on its possible content of halogen atoms either naturally occurring or (more likely) where a substitution can be made without affecting waxing properties. |
| $^{131}$I | 8.02 d | $\beta^-$-emission-two main energies: $E1_{\beta max} = 606.3$ keV (89.9%), $E2_{\beta max} = 333.8$ keV (7.3%) $\gamma$-radiation-main energy in keV: 364.5 (81.7%) | Reactor irradiation: 1: Fission of $^{235}$U 2: $^{130}$Te(n,$\gamma$)$^{131}$Te $\Rightarrow$ $\beta^-$ decay to $^{131}$I Commercially available | The relevance of $^{131}$I-label in a wax molecule depends on its possible content of halogen atoms either naturally occurring or (more likely) where a substitution can be made without affecting waxing properties. |

The Stable Isotope Label

TABLE 3

Some information on stable isotopic labels

| Stable nuclide | Comments |
|---|---|
| $^2$H (D) | The fraction of deuterium in natural hydrogen is 0.015%. This means that, in average, out of one million hydrogen atoms 150 will be deuterium. Exchanging hydrogen with deuterium to a degree $\approx$ 10% (e.g. 5 to 90%, preferably 10 to 80%, such as 10 to 30%) in wax molecules will be sufficient for a good wax tracer without essentially changing the molecular properties. |
| $^{13}$C | The fraction of $^{13}$C in natural carbon is 1.10%. A good wax tracer based on this carbon isotope should contain as many $^{13}$C-atoms as possible, preferably at least 20% (e.g.20 to 99%), more preferably at least 50% or at least 70%. |
| $^{15}$N | The fraction of $^{15}$N in natural nitrogen is 0.366%. The relevance of $^{15}$N-label in a wax molecule depends on its possible content of N-atoms, for instance in attached amine (—NH$_2$) groups. |
| $^{18}$O | The fraction of $^{18}$O in natural oxygen is 0.200%. The relevance of $^{18}$O-label in a wax molecule depends on its possible content of O-atoms, for instance in attached acidic (—COOH) groups, on alcohol groups (—OH), ketones or others. |
| $^{34}$S | The fraction of $^{34}$S in natural sulphur is 4.21%. The relevance of $^{34}$S-label in a wax molecule depends on its possible content of S-atoms, for instance in attached sulphate (—O—SO$_3$H) or sulphonic acid (—SO$_3$H) groups. |

The Fluorescent Label

Fluorescent labelling is accomplished using a chemically reactive derivative of a fluorophore. Many types of fluorophores exist. It is not practical to present such a list here. Therefore, see reference list below for appropriate web addresses. A few examples of common reactive groups include:

Isothiocyanate derivatives such as FITC and TRITC (derivatives of fluorescein and rhodamine), see Formulae I and II. They are reactive towards primary amines in a waxy molecule to form a thioureido linkage between the wax molecule and the fluorescent dye.

Formula I

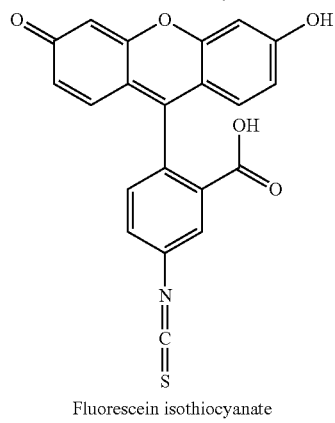

Fluorescein isothiocyanate detivative (FITC)

Formula II

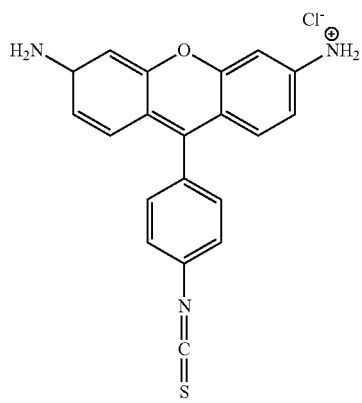

Rhodamine isothiocyanate derivative (TRITC)

Succinimidyl esters such as NHS-fluorescein (Formula III). They are reactive towards amino groups to form an amido bond.

Formula III

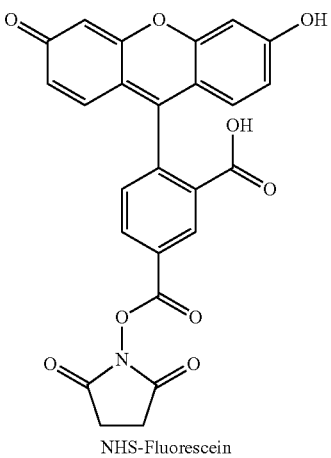

NHS-Fluorescein

Reaction of such reactive dyes with another (especially a wax) molecule results in a stable covalent bond formed between a fluorophore and a labelled molecule.

Following a fluorescent labelling reaction, it is often necessary to remove any nonreacted fluorophore from the labelled target molecule. This may be accomplished by size exclusion chromatography, taking advantage of the size difference between fluorophore and labelled wax molecule.

Reactive fluorescent dyes are commercially available. They can be obtained with different reactive groups for attachment to various functional groups within a wax molecule. They are also available in labelling kits that contain all the components to carry out a labelling reaction.

In the present invention, the concentration of labelled wax is measured at at least one out-flow point. Such a concentration measurement may be made by any of the techniques described herein, such as GC-MS, radiation detection or fluorescence detection. The concentration of wax may be measured as an "absolute" value, by measurement of the labelled wax. This may be compared with the amount injected and with standard curves or using a known dilution factor to provide information on how much labelled wax has precipitated in the transport system.

Alternatively, a "relative" concentration measurement may be made by including a second, non-precipitating component. Such a non-precipitating component may optionally be added simultaneously with the labelled wax and at a known concentration relative to that labelled wax. By taking a "relative" measurement of labelled wax concentration in comparison with the concentration of non-precipitating component, the degree of precipitation of the labelled wax may be determined. This assessment can be made without exact knowledge of the level of dilution or the precise amount injected because the non-precipitating component will act as an internal standard against which the labelled wax is measured.

A key aspect of the present invention is the injection of the labelled wax "tracers" into the well-stream. Injection points include wellhead, upstream chokes, tie-ins or other areas where the system sees pressure or temperature changes. Injection of the tracer can be done using existing infrastructure such as service lines, MEG injection lines or other injection lines available in the system.

By choosing the correct molecule based on pre-studies of the wax forming for each specific system the tracer molecule should precipitate with the wax. Identification of the wax component to be used can be done by chromatography such as GC or GC-MS, or similar methods [8]. This analysis will identify all relevant wax components. This includes linear, branched and cyclic alkanes that might be part of the precipitating wax. The wax to be characterized may be found through precipitation experiments.

Relevant wax for characterization can be identified through wax appearance and wax deposition testing. Actual crude/condensate from the field where the tracer shall be used or oil with comparable properties should be used in the precipitation testing. The wax component needs to be chosen so that it will precipitate to an extent to where the difference between components injected and lost is measurable. Several labelled wax molecules might be used in combination, each specifically chosen to co-precipitate with the relevant wax molecules of the natural sample. Care will be taken to make sure the wax tracers used will not precipitate by itself. Compatibility testing of the oil, wax tracer and any other chemicals added to the system may therefore be necessary.

The detection of the amount of wax deposited can be done either at the sample point or by careful sampling followed by ex-situ monitoring.

It is foreseeable that an online measurement unit can be constructed in order to enable continuous monitoring. This might be desired in extreme situations where the time from onset of wax deposition and blocking of the pipeline/equipment is short.

In addition to the generation and use of precipitating labelled wax tracers it is suggested that a reference molecule (labelled non-precipitating component) is injected alongside the wax tracer. This might be a regular oil tracer or a custom molecule created during the wax tracer production. Any molecule that can be traced can be used as long as no precipitation of the molecule is expected. Reference molecules might also be used where precipitation rate and characteristics are known but some precipitation does take place.

A sketch showing the basic principle of the injection and analysis scheme is seen in FIG. 4. The sketch is provided as an example of a simplified system and many other designs and implementations will be evident to the skilled worker. The system is applicable to both floating production systems and systems with onshore processing of the produced fluids.

The following are three example tracer injection methods:

i. Pulse injection: A well-known amount of labelled wax (tracer) is dissolved in a known small (a few liters, such as 1 to 10 liters) liquid (L1) volume with relatively high tracer concentration. The liquid L1 is chemically compatible with the fluid transported in the pipeline. This tracer-labelled volume is injected by high-pressure displacement pumps as a slug in a short period of time (e.g. 10 seconds to 30 minutes). The tracer slug is optionally followed by a few liters (e.g. 1 to 10 liters) of non-labelled liquid L1 to rinse out any remaining traces of the tracer liquid from the injection tubing to make ready for another tracer pulse injection at a later time. The pumps needed here are ordinary high-pressure tracer injection or chemical injection pumps. The injection principle is illustrated in FIG. 5a.

ii. Continuous injection: Labelled wax (tracer) molecules are dissolved to a known but diluted concentration in a liquid which is compatible with the fluid in the pipeline. The labelled volume may be several hundred liters (e.g. 100 to 1000 liters). For steady state flow in the pipeline, injection is carried out at constant volumetric rate with a small-volume high-pressure metering pump (for instance an HPLC pump). Thus, tracer is injected in a constant concentration. In cases where there are time differences in the pipeline volumetric flow rate, the injection rate should be controlled by feedback from the log of the pipeline flow rate in order to maintain a constant concentration of the tracer at the injection point. A variation of this injection regime is the so-called square-pulse injection where a constant concentration is maintained for some minutes, hours or days. Such a square-pulse injection may be repeated at intervals. The injection principle is illustrated in FIG. 5b.

iii. Continuous dissolution and injection: This procedure requires that the tracer wax molecules exist in the solid (precipitated) form. The solid is encapsulated in such a way that part of its surface is exposed to a liquid L2 which upon contact with the solid may dissolve wax, and thereby wax tracer molecules, from the solid surface. The liquid L2 is also chemically compatible with the fluid in the pipeline. Dissolution is slow, but sufficient to create a well detectable tracer concentration in the fluid in the liquid L2 which flows over the exposed solid surface. The same type of pump as described in section ii. above may be used here. The concentration of the tracer in the injection fluid will not be exactly constant in time. The concentration depends on the shape of the exposed surface. However, for fluorescent or radiolabelled tracers, this concentration can be continuously logged in specially designed measurement cells on the injection tubing. The fluorescent tracers will be analysed with light- and/or laser-induced fluorescence and the radiotracers with either gamma spectrometry or solid scintillation counting where the solid scintillator consists of a detector cell filled with scintillating glass or plastic pellets in contact with the continuously flowing tracer-containing injection fluid. The injection principle and attached monitoring system is illustrated in FIG. 5c.

In each of the cases i, ii and iii, the solvent (or dissolving liquid) may contain a component which can operate as a passive tracer for the pipeline flow.

Interpretation of Measurements

Interpretation of results from pulse injection experiments are in praxis performed by so-called moment analysis normally used in Residence-Time-Distribution (RTD) experiments. Here, the total integral under the recorded tracer production curve and the shape of the curve are parameters to be considered. This method is regarded as well-known, and will not be further detailed here. Comparison with a possible co-injected passive tracer may also indicate the degree of chromatographic behavior of wax molecules throughout the transportation process in the pipeline.

Interpretation of results from the continuous injection method is straight forward: Providing steady state in the transportation pipeline, the tracer concentration in the exit fluid reaches a constant concentration level which is lower than the injected concentration. The difference has been irreversibly precipitated in the pipeline. In cases where a square-pulse injection has been performed, additional information on the precipitation and flow structure may be found in the front and tail of the production profile.

In case iii above where wax tracer is continuously dissolved from a preformed wax precipitate and subsequently injected, the interpretation process is somewhat more complicated. Here, one needs to take into account the actually injected concentrations as measured on-line by the nuclear or fluorescent detection equipment. However, this calculation will be within the capacity of the skilled worker.

For all cases, the simultaneous application of two or more wax tracer molecules with different precipitation properties (or deposition temperature) will further indicate real deposition temperatures in the pipeline and also give information on the total wax deposition kinetics. Such information is important to decide about the need for a pigging operation.

In addition to the abovementioned novel wax tracing method, a corresponding monitoring technique can be used for monitoring of precipitation of asphaltenes. Such materials are potentially also a threat to the stable operation of a fluid transport system since they can precipitate, particularly in vicinity of the well head. By utilizing a similar methodology for identification of tracer and labelling of the identified specie the technique will be able to detect onset and precipitation rate of asphaltenes using labelling and analytical techniques corresponding to those disclosed herein for wax. The chemical structure of asphaltenes differs from that of wax due to multiple fused aromatic rings and the presence of heteroatomic species such as oxygen, nitrogen and metal atoms in the structure [6]. However, the procedure for identification of a suitable tracer molecule or population of tracers may be readily based on those disclosed herein for waxes to enable labelling of appropriate asphaltenes. This evidently forms further aspects of the invention, corresponding to those aspects disclosed herein for wax.

CITATIONS

[1] S. Suppiah, A. Ahmad, C. Alderson, K. Akbarzadeh, J. Gao, J. Shorthouse, I. A. Khan, C. Forde, A. Jamaluddin, Oil and Gas Facilities, 2 (2012).

[2] H. A. Craddock, K. Mutch, K. Sowerby, S. W. McGregor, J. Cook, C. Strachan, A Case Study in the Removal of Deposited Wax From a Major Subsea Flowline System in the Gannet Field, in: International Symposium on Oilfield Chemistry, Society of Petroleum Engineers, Houston, Tex., U.S.A., 2007.

[3] K. Akbarzadeh, J. Ratulowski, D. Eskin, T. Davies, SPE Projects, Facilities & Construction, 5 (2010) pp. 49-57.

[4] P. Manfield, W. Nisbet, J. Balius, G. Broze, L. Vreenegoor, "Wax-On, Wax-Off": Understanding and Mitigating Wax Deposition in a Deepwater Subsea Gas/Condensate Flowline, in: Offshore Technology Conference, Houston, Tex., 2007.

[5] D. J. Bilyeu, T. X. Chen, Clearing Hydrate and Wax Blockages in a Subsea Flowline, in: Offshore Technology Conference, Houston, Tex., 2005.

[6] Diallo M S, Cagin T, Faulon J L, Goddard III W A. 2000. Thermodynamic properties of asphaltenes: a predictive approach based on computer assisted structure elucidation and atomistic simulations. Elsevier Science. 40:103-127

[7] H. Alboudwarej, Z. Huo, E. C. Kempton, Flow-Assurance Aspects of Subsea Systems Design for Production of Waxy Crude Oils, in: SPE Annual Technical Conference and Exhibition, Society of Petroleum Engineers, San Antonio, Tex., USA, 2006.

[8] P. Marriott, Journal of Separation Science, 27 (2004) 1360-1360.

BRIEF SUMMARY OF THE FIGURES

FIG. 1 shows examples of molecular classes which can be used as precursors for labelling operations.

FIG. 2 shows an outline of a test apparatus suitable for testing and validation of potential labelled waxes (tracers).

FIG. 3: shows various possible methods for labelling an example wax molecule. 1. Is the unlabeled wax molecule, 2. to 7. represent the molecule with various labels: 2. tritium-labeled, 3. $^{14}C$-labeled, 4. $^{131}I$-labeled, 5. $^{13}C$-substituted, 6. deuterium-substituted and 7. Functional group attached.

FIG. 4: shows one potential layout of a production system where it is suggested that wax tracers are injected through a chemicals injection line to the wellhead or tie-in junction. By monitoring the traces produced to onshore facilities or to another offshore installation the initiation and magnitude of the waxing can then be monitored. In addition to the transport lines wax tracers can be used to monitor deposition in process equipment.

The markings in FIG. 4 are as follows:
1—Riser
2—Transport pipeline (fluid transport system)
3—Tracer injection line.
4—Production well.
5—Well/head.
6—Multiphase separator.
7—Analysis Point.
8—Reservoir section 1.
9—Reservoir section 2.
10—Sealing fault.

FIG. 5a. shows a sketch of wax tracer pulse injection system.

FIG. 5b. shows a sketch of wax tracer injection system for continuous constant concentration injection.

FIG. 5c. shows a sketch of wax tracer injection system for continuous dissolution of preformed wax precipitate containing wax tracer molecules with detectors for continuous logging of injected tracer concentration.

EXAMPLES

Example 1—Study of Wax Deposition

Deposition of waxy components is studied in dynamic flooding experiments in the laboratory where wax-containing condensates are pumped through steel tubes packed with steel wool to increase the contact surface. Deposition of gamma emitting wax tracers are detected directly on the outside of the steel tubing with a gamma detector. Wax molecules labeled with beta-emitting tracers or with fluorescent labels are analysed in the collected fluid at the exit of the flow rig. Two procedures are applied: 1. The liquid is pumped through the equipment only once, i.e. the internal walls of the flow loop are continuously contacted with fresh wax-containing condensate at constant concentration. 2. The condensate is recycled without any solute addition. In these experiments parameters are temperature, wax type and concentration and tracer type. A principle sketch is shown in FIG. 2.

The invention claimed is:

1. A method for monitoring precipitation of at least one wax component from a hydrocarbon-containing fluid stream flowing through a fluid transport system having at least one in-flow point and at least one out-flow point, the method comprising:
   a) taking a sample of the hydrocarbon-containing fluid stream;
   b) analyzing the sample of the hydrocarbon-containing fluid;
   c) identifying at least one of a group consisting of a structure and molecular weight of at least one wax component in the sample of the hydrocarbon-containing fluid;
   d) selecting or generating at least one labelled wax based upon the structure or molecular weight of the at least one wax component identified in step c), wherein the selected or generated at least one labeled wax is labeled with either an isotope label or with a covalently attached label;
      i) introducing the at least one labelled wax selected or generated in step d) into the hydrocarbon-containing fluid stream at the at least one in-flow point; and
      ii) measuring a relative or absolute concentration of the at least one labelled wax in at least one sample taken at the at least one out-flow point.

2. The method of claim 1, wherein step a) comprises taking a sample of the hydrocarbon-containing fluid stream at a point selected from at least one of a group consisting of an in-flow point of the fluid transport system, an out-flow point of the fluid transport system, another point on the fluid transport system and at a production point within a formation during at least one of a group consisting of production, development and exploration.

3. The method of claim 1, wherein the at least one labelled wax is to precipitate alongside the at least one wax component precipitating from the hydrocarbon-containing fluid stream.

4. The method of claim 1, wherein the structure of at least one wax component is identified in step c) and the at least one labelled wax is selected or generated in step d) to have a structure comprising the structure of the at least one wax component identified in step c) and at least one label.

5. The method of claim 1, further comprising undertaking at least one wax mitigation measure when the relative or absolute concentration measured in step ii) falls below a threshold value.

6. The method of claim 5, wherein the at least one wax mitigation measure comprises at least one of a group consisting of starting or increasing an addition of at least one de-waxing component to the hydrocarbon-containing fluid stream, mechanically de-waxing at least a part of the fluid transport system, and thermally de-waxing at least a part of the fluid-transport system.

7. The method of claim 1, further comprising undertaking at least one wax mitigation measure when an integral of a curve of relative or absolute concentration measured in step ii) against time for a predetermined period falls below a threshold value.

8. The method of claim 1, wherein step i) is carried out one of periodically and continuously.

9. The method of claim 1, wherein step ii) is carried out one of periodically and continuously.

10. The method of claim 1, wherein step i) is carried out periodically for at least 1 year following an event selected from at least one of a group consisting of a change or partial change in source of the hydrocarbon-containing fluid stream, at least one from a group consisting of the addition, removal and replacement of at least one element of the fluid transport system, at least one from the group consisting of an addition, removal and change in concentration of at least one additive introduced into the hydrocarbon-containing fluid stream, and a change in conditions of at least one from a group consisting of temperature and pressure at at least one point on the fluid transport system.

11. The method of claim 1, wherein the fluid transport system comprises at least one from a group consisting of a pipeline, a valve, a choke, a separator, filters, mixers, joints, thermal expansion joints, and tie-inns.

12. The method of claim 1, wherein the at least one labelled wax and at least one labelled non-precipitating component are introduced in step i) at a known relative concentration and step ii) comprises measuring the relative concentration of the at least one labelled wax and the at least one labelled non-precipitating component in the at least one sample.

13. The method of claim 1, wherein the at least one labelled wax is labelled by means of a radioactive isotope selected from at least one of a group consisting of $^3H$, $^{14}C$, $^{35}S$, $^{32}P$, $^{125}I$, $^{131}I$ and $^{82}Br$.

14. The method of claim 1, wherein the at least one labelled wax is labelled by means of at least one of a group consisting of a radioactive isotope, a non-radioactive heavy isotope selected from at least one from a group consisting of $^{2}H$, $^{13}C$, $^{15}N$, $^{18}O$ and $^{34}S$ and a covalently attached fluorophore.

15. The method of claim 1, wherein the precipitation of the at least one wax component from a hydrocarbon-containing fluid stream flowing through a fluid transport system having at least one in-flow point and at least one out-flow point is monitored by monitoring precipitation of the at least one labelled wax.

16. A method for the generation of at least one labelled wax comprising:
 a) taking a sample of a hydrocarbon-containing fluid stream;
 b) analyzing the sample of the hydrocarbon-containing fluid;
 c) identifying at least one of a group consisting of a structure and molecular weight of at least one wax component in the sample of the hydrocarbon-containing fluid;
 d) selecting a wax based upon the structure or molecular weight of the at least one wax component identified in step c); and
 e) covalently or isotopically modifying the selected wax with at least one label.

17. The method of claim 16, wherein step a) comprises taking a sample of the hydrocarbon-containing fluid stream at a point selected from at least one of a group consisting of an in-flow point of a fluid transport system, an out-flow point of a fluid transport system, another point of a fluid transport system, and at a production point within a formation during at least one from a group consisting of production, development and exploration.

* * * * *